(12) United States Patent
Brunet et al.

(10) Patent No.: US 7,737,176 B2
(45) Date of Patent: Jun. 15, 2010

(54) SUBSTITUTED ARYLHEXADIENOIC ACIDS AND ESTERS THEREOF WHICH CAN BE USED FOR THE TREATMENT AND PREVENTION OF DIABETES, DYSLIPIDAEMIA AND ATHEROSCLEROSIS, PHARMACEUTICAL COMPOSITIONS COMPRISING THEM AND PROCESSES FOR THE PREPARATION OF THEM

(75) Inventors: Michel Brunet, Toussieu (FR); Jean-Jacques Zeiller, Lyons (FR); Gérard Ferrand, Lyons (FR); Yves Bonhomme, Charbonnieres les Bains (FR)

(73) Assignee: Merck Patent GmbH, Darmstadt (DE)

( * ) Notice: Subject to any disclaimer, the term of this patent is extended or adjusted under 35 U.S.C. 154(b) by 1475 days.

(21) Appl. No.: 10/530,022

(22) PCT Filed: Aug. 11, 2003

(86) PCT No.: PCT/EP03/08887

§ 371 (c)(1),
(2), (4) Date: Apr. 1, 2005

(87) PCT Pub. No.: WO2004/031116

PCT Pub. Date: Apr. 15, 2004

(65) Prior Publication Data
US 2006/0052447 A1    Mar. 9, 2006

(30) Foreign Application Priority Data
Oct. 1, 2002    (FR) .................................. 02 12135

(51) Int. Cl.
A61K 31/38    (2006.01)
A61K 31/20    (2006.01)
C07C 69/00    (2006.01)
C07C 59/00    (2006.01)

(52) U.S. Cl. ...................... 514/443; 514/571; 560/62; 560/59; 562/466; 562/472

(58) Field of Classification Search ............... 514/443, 514/571; 560/59, 62; 562/466, 472
See application file for complete search history.

(56) References Cited

U.S. PATENT DOCUMENTS 7,465,752 B2 *    12/2008    Zeiller et al. ................. 514/443
7,482,484 B2 *    1/2009    Adje et al. ................... 562/466

FOREIGN PATENT DOCUMENTS

RU    2051673    1/1996

OTHER PUBLICATIONS

Randle et al. (Lancet, 1963, 785-789).
Lehmann, J.M. et al: An Antidiabetic Thiazolidinedione is a High Affinity Ligand for Peroxisome Proliferator-Activated Receptro (PPAR) The Journal of Biological Chemistry, vol. 270, No. 22, 1995, pp. 12953-12956, XP002228130.
Database WPI Section Ch, Week 199642 Derwent Publications Ltd., London, GB; AN 1996-423454 XP002228131.

* cited by examiner

Primary Examiner—Sabiha Qazi
(74) Attorney, Agent, or Firm—Millen, White, Zelano & Branigan, P.C.

(57) ABSTRACT

The invention relates to compounds of the formula I:

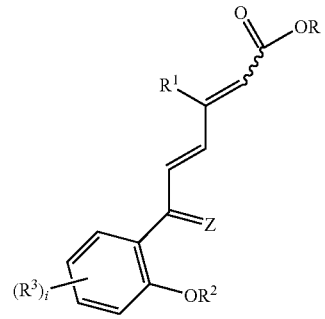

and to the pharmaceutically acceptable salts thereof, to processes for the preparation of them and to pharmaceutical compositions comprising them, which are useful especially for the treatment and prevention of dyslipidaemia, atherosclerosis and diabetes.

3 Claims, No Drawings

SUBSTITUTED ARYLHEXADIENOIC ACIDS AND ESTERS THEREOF WHICH CAN BE USED FOR THE TREATMENT AND PREVENTION OF DIABETES, DYSLIPIDAEMIA AND ATHEROSCLEROSIS, PHARMACEUTICAL COMPOSITIONS COMPRISING THEM AND PROCESSES FOR THE PREPARATION OF THEM

The present invention relates to arylhexadienoic acid derivatives that can be used in the treatment of dyslipidaemia, atherosclerosis and diabetes, to pharmaceutical compositions comprising them, and to processes for the preparation of these compounds.

The invention also relates to the use of these compounds for the production of medicaments intended for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease remain the prime cause of death and handicap throughout the world.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform).

In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., 1995, 270, 12953-12956).

The inventors have discovered a novel class of compounds that are powerful activators of the PPARα and PPARγ isoforms. On account of this activity, these compounds have a considerable hypolipidaemiant and hypoglycaemiant effect.

More specifically, the compounds I of the invention have the formula:

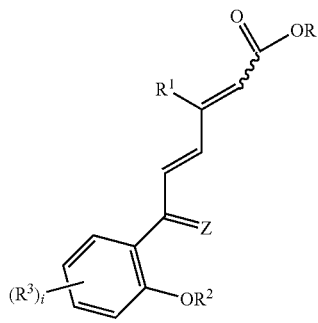

in which $R^1$ represents an optionally substituted saturated aliphatic hydrocarbon-based group; an optionally substituted saturated and/or aromatic carbocyclic group; an optionally substituted saturated and/or aromatic heterocyclic group;

$R^2$ represents an optionally halogenated saturated aliphatic hydrocarbon-based group; an optionally substituted saturated and/or aromatic carbocyclic group; a saturated aliphatic hydrocarbon-based group which is substituted by an optionally substituted aromatic carbocyclic group; or a saturated aliphatic hydrocarbon-based group which is substituted by a saturated and/or aromatic heterocyclic group;

the radicals $R^3$ represent, independently of each other, a saturated aliphatic hydrocarbon-based group, which is optionally halogenated and/or optionally interrupted by one or more O or S atoms; a halogen atom; a nitro group; cyano; a $(C_6\text{-}C_{10})$aryloxy group, which is optionally substituted by one or more radicals G°; a $(C_6\text{-}C_{10})$arylthio group, which is optionally substituted by one or more radicals G°; $(C_1\text{-}C_{10})$alkylsulfonyl; $(C_6\text{-}C_{10})$arylsulfonyl, in which aryl is optionally substituted by one or more radicals G°; 5- to 7-membered heteroaryl which comprises one or more hetero atoms chosen from O, N and S and is optionally substituted by one or more radicals G°; $(C_6\text{-}C_{10})$aryloxycarbonyl; $(C_6\text{-}C_{10})$-arylcarbonylamino; $(C_1\text{-}C_{10})$alkoxycarbonyl; $(C_1\text{-}C_{10})$alkylcarbonylamino; di$(C_1\text{-}C_{10})$alkylamino; $(C_6\text{-}C_{10})$aryl$(C_1\text{-}C_{10})$alkyl, in which aryl is optionally substituted by one or more radicals G°; $(C_6\text{-}C_{10})$aryl, which is optionally substituted by one or more radicals G°; $(C_1\text{-}C_{10})$alkylcarbonyl; or $(C_3\text{-}C_8)$cycloalkyl$(C_1\text{-}C_{10})$alkyl, in which cycloalkyl is optionally substituted by one or more radicals G°; G° is chosen from halogen; optionally halogenated alkoxy; or optionally halogenated alkyl;

R represents a hydrogen atom; a saturated aliphatic hydrocarbon-based group; an amino group, which is optionally substituted by one or two saturated aliphatic hydrocarbon-based groups; or an optionally substituted aromatic carbocyclic group;

Z represents O; CHR⁴, in which R⁴ takes any of the meanings given above for R;

i represents the integer 0, 1, 2, 3 or 4, and also the pharmaceutically acceptable salts thereof.

According to the invention, the term "halogen atom" means a chlorine atom, a bromine atom, a fluorine atom or an iodine atom.

The term "aliphatic hydrocarbon-based group" means a hydrocarbon-based group having a linear or branched chain, preferably containing from 1 to 14 carbon atoms, preferentially from 1 to 10 and better still from 1 to 6 carbon atoms, for example from 1 to 4 carbon atoms.

Examples of saturated hydrocarbon-based aliphatic groups are alkyl radicals, such as methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

Examples of halogenated saturated hydrocarbon-based aliphatic groups are haloalkyl groups, such as perhaloalkyl groups of —$CF_3$, —$CF_2$—$CF_3$, —$CCl_3$ or —$CCl_2$—$CCl_3$ type.

In the context of the invention, the expression "saturated and/or aromatic cyclic (carbocyclic or heterocyclic) radical" means that the same radical may comprise a saturated portion and/or an aromatic portion.

The carbocyclic and heterocyclic radicals include mono- and polycyclic radicals; these radicals preferably denote mono-, bi- or tricyclic radicals. In the case of polycyclic radicals, it should be understood that these radicals consist of monocycles fused in pairs (for example ortho-fused or peri-fused), i.e. containing at least two carbon atoms in common. Each monocycle is preferably 3- to 8-membered and better still 5- to 7-membered.

The heterocyclic groups comprise hetero atoms generally chosen from O, N and S optionally in oxidized form (in the case of S and N).

Each of the monocycles constituting the heterocycle preferably comprises from 1 to 4 hetero atoms and better still from 1 to 3 hetero atoms.

Examples of aromatic monocyclic heterocyclic groups are 5- to 7-membered monocyclic heteroaryls, such as pyridine, furan, thiophene, pyrrole, imidazole, thiazole, isoxazole, isothiazole, furazane, pyridazine, pyrazine, thiazines, oxazole, pyrazole, oxadiazole, triazole and thiadiazole.

Examples of unsaturated monocyclic heterocyclic groups are unsaturated derivatives of the aromatic monocyclic heterocycles mentioned above.

Examples of saturated 5- to 7-membered monocyclic heterocycles are especially tetrahydrofuran, dioxolane, imidazolidine, pyrazolidine, piperidine, dioxane, morpholine, dithiane, thiomorpholine, piperazine, trithiane, oxepine and azepine.

Examples of aromatic bicyclic heterocyclic groups in which each monocycle is 5- to 7-membered are indolizine, indole, isoindole, benzofuran, benzopyran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

The saturated derivatives of these groups are examples of saturated bicyclic heterocyclic groups.

Examples of aromatic tricyclic heterocyclic groups are those consisting of 5- to 7-membered monocycles, such as acridine or le carbazole. The saturated derivatives of these groups are examples of saturated tricyclic heterocyclic groups.

The aromatic carbocyclic radicals are preferably ($C_8$-$C_{18}$).

Among these radicals, mention may be made especially of phenyl, naphthyl, anthryl and phenanthryl radicals.

An example of a saturated aliphatic hydrocarbon-based group substituted by an optionally substituted aromatic group that may be mentioned is the optionally substituted benzyl group.

Saturated carbocyclic radicals are especially cycloalkyl radicals, preferably ($C_3$-$C_{18}$)cycloalkyl and better still ($C_3$-$C_{10}$)cycloalkyl, such as cyclopropyl, cyclobutyl, cyclopentyl, cyclohexyl, cycloheptyl, cyclooctyl, adamantyl or norbornyl.

Examples of aromatic and/or saturated carbocyclic nuclei are the following radicals:

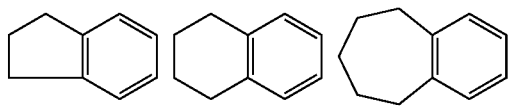

Examples of saturated and/or aromatic heterocyclic nuclei are the following radicals:

B1:

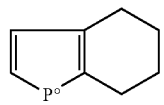

B2:

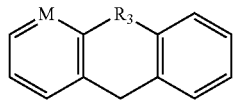

B3:

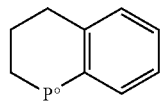

B4:

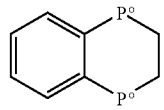

B5:

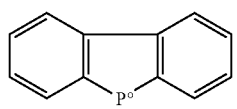

B6:

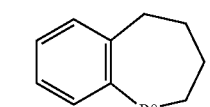

B7:

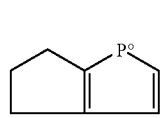

in which P° represents O, S or $SO_2$ and M represents N or C. Preferably, in B1, P° represents O or S; in B2, P° represents $SO_2$ or O and M represent C or N; in B3, P° represents O; in B4, P° represents O; in B5, P° represents O; in B6, P° represents O; in B7, P° represents S.

If M or P° represents N, this atom is preferably substituted by a hydrogen atom or with alkyl or alkylcarbonyl.

If the optionally halogenated saturated aliphatic hydrocarbon-based group is interrupted by one or more oxygen or sulfur atoms, this means that one or more carbon atoms of the hydrocarbon-based chain are replaced by one or more oxygen or sulfur atoms, it being understood that two hetero atoms are not linked together in the chain.

$R^1$ preferably represents alkyl or aryl, for example ($C_1$-$C_6$) alkyl, such as methyl or ($C_6$-$C_{10}$)aryl, such as phenyl.

A preferred meaning of Z is O.

Advantageously, i is 1 and $R^3$, located in position 5 of the phenyl nucleus, represents ($C_1$-$C_6$)alkyl, ($C_1$-$C_6$)alkoxy or a halogen atom.

Advantageously, $R^2$ represents ($C_1$-$C_6$)alkyl or benzyl.

The substituents on the aliphatic hydrocarbon-based groups, carbocyclic groups and heterocyclic groups are, for example:

a halogen atom; cyano; hydroxyl; nitro; optionally halogenated ($C_1$-$C_{10}$)alkyl; optionally halogenated ($C_1$-$C_{10}$) alkoxy; ($C_6$-$C_{10}$)alkylthio, which is optionally substituted by ($C_6$-$C_{10}$)arylsulfonyl, in which aryl is optionally substituted by one or more radicals G; ($C_6$-$C_{10}$)aryloxy, in which aryl is optionally substituted by one or more radicals G; ($C_6$-$C_{10}$)arylthio, in which aryl is optionally substituted by one or more radicals G; ($C_1$-$C_{10}$)alkylsulfonyl; ($C_6$-$C_{10}$)arylsulfonyl, in which aryl is optionally substituted by one or more radicals G; 5- to 7-membered heteroaryl which comprises one or more hetero atoms chosen from O, N and S and is optionally substituted by one or more radicals G and/or with ($C_1$-$C_{10}$)alkylcarbonyl; ($C_1$-$C_{10}$)alkoxycarbonyl; ($C_6$-$C_{10}$)aryloxycarbonyl, in which aryl is substituted by one or more radicals G; ($C_1$-$C_{10}$)alkylcarbonylamino; di($C_1$-$C_{10}$)alkylamino; ($C_2$-$C_4$)alkylenedioxy; ($C_3$-$C_5$) alkylene, which is optionally substituted by oxo; ($C_6$-$C_{10}$) aryl($C_1$-$C_{10}$)alkyl, in which aryl is optionally substituted by one or more radicals G; ($C_6$-$C_{10}$) aryl, which is optionally substituted by one or more radicals G; ($C_1$-$C_{10}$)alkylcarbonyl, preferably ($C_1$-$C_6$)alkylcarbonyl; ($C_3$-$C_8$)cycloalkyl($C_1$-$C_8$)alkyl, in which cycloalkyl is itself substituted by ($C_6$-$C_{10}$)arylsulfonylamino, in which aryl is optionally halogenated;

in which G is chosen from halogen; hydroxyl; optionally halogenated ($C_1$-$C_{14}$)alkoxy, preferably optionally halogenated ($C_1$-$C_{10}$)alkoxy; optionally halogenated ($C_1$-$C_{14}$) alkyl, preferably optionally halogenated ($C_1$-$C_{10}$)alkyl; nitro; cyano; di($C_1$-$C_{14}$)alkylamino, preferably di($C_1$-$C_{10}$) alkylamino; ($C_6$-$C_{10}$)aryl, which is optionally halogenated and/or optionally substituted by ($C_1$-$C_{14}$)alkyl.

Examples of halogenated saturated aliphatic hydrocarbon-based groups (or haloalkyl groups) are perhalo groups, such as trifluoromethyl or 2,2,3,3,3-pentafluoroethyl.

Similarly, an example of a haloalkoxy group is a perhalogenated group, such as trifluoromethoxy.

The salts of compounds of the formula I of the invention containing a basic function can be obtained by addition with an acid, for example by reacting the compound of the formula I with an equivalent amount of the acid in an inert solvent, such as ethanol, and subsequent evaporation. Acids that are particularly suitable include organic or mineral acids that produce physiologically acceptable salts.

Mineral acids that may be mentioned include sulfuric acid, nitric acid, hydrohalic acids, such as hydrochloric acid or hydrobromic acid, phosphoric acids, such as orthophosphoric acid, and sulfamic acid.

Suitable organic acids that will be mentioned in particular include monobasic or polybasic aliphatic, alicyclic, araliphatic, aromatic or heterocyclic, carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, para-toluenesulfonic acid, naphthalenemono- and -disulfonic acids, and laurylsulfuric acid.

The salts with acids that are not physiologically acceptable are, for example, the picrates, which can be used in the context of the present invention for the isolation and/or purification of the compounds of the formula I.

The compounds of the formula I containing at least one acid function can be converted into the corresponding salts thereof by reaction with a physiologically acceptable organic base, for instance ethanolamine.

They can also be converted into corresponding metal salts, in particular alkali metal or alkaline-earth metal salts or into ammonium salts, by reaction with bases, such as potassium hydroxide, sodium hydroxide or a carbonate.

A first preferred subgroup of compounds of the invention consists of the compounds of the formula I in which:

$R^1$ represents an optionally substituted saturated aliphatic hydrocarbon-based group; an optionally substituted saturated and/or aromatic carbocyclic group;

$R^2$ represents an optionally halogenated saturated aliphatic hydrocarbon-based group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, optionally halogenated and/or optionally interrupted by one or more O or S atoms; a halogen atom; an optionally halogenated ($C_1$-$C_{10}$) alkoxy group; a ($C_6$-$C_{10}$)aryl group, which is optionally substituted by one or more radicals G°; a 5- to 7-membered heteroaryl group which comprises one or more hetero atoms chosen from O, N and S and optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones more particularly preferred are those which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl.

Among these compounds, the ones that are especially distinguished are the compounds for which $R^2$ represents $C_1$-$C_{10}$ alkyl. The compounds for which $R^2$ represents benzyl are also distinguished.

A second preferred subgroup of compounds of the invention consists of the compounds of the formula I in which:

$R^1$ represents an optionally substituted saturated and/or aromatic heterocyclic group;

$R^2$ represents an optionally halogenated saturated aliphatic hydrocarbon-based group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, which is optionally halogenated and/or optionally interrupted by one or more O or S atoms; a halogen atom; an optionally halogenated ($C_1$-$C_{10}$)alkoxy group; a ($C_6$-$C_{10}$)aryl group, which is optionally substituted by one or more radicals G°; a 5- to 7-membered heteroaryl group which comprises one or more hetero atoms chosen from O, N and S and optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A third preferred subgroup of compounds of the invention consists of the compounds of the formula I in which:

$R^1$ represents an optionally substituted saturated and/or aromatic carbocyclic group; or an optionally substituted saturated and/or aromatic heterocyclic group;

$R^2$ represents an optionally halogenated saturated aliphatic hydrocarbon-based group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, which is optionally halogenated and/or optionally interrupted by one or more O or S atoms; a halogen atom; an optionally halogenated ($C_1$-$C_{10}$)alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A fourth preferred subgroup of compounds of the invention consists of the compounds of the formula I in which:

$R^1$ represents an optionally substituted saturated aliphatic hydrocarbon-based group; an optionally substituted saturated and/or aromatic heterocyclic group;

$R^2$ represents an optionally halogenated aliphatic hydrocarbon-based group; or a saturated aliphatic hydrocarbon-based group which is substituted by an optionally substituted aromatic group;

the radicals $R^3$ are as generally defined above or better still the radicals $R^3$ represent, independently of each other, a saturated aliphatic hydrocarbon-based group, which is optionally halogenated and/or optionally interrupted by one or more O or S atoms; a halogen atom; an optionally halogenated ($C_1$-$C_{10}$)alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A fifth preferred subgroup of compounds of the invention consists of the compounds of the formula I in which:

$R^1$ represents an optionally substituted saturated aliphatic hydrocarbon-based group; an optionally substituted saturated and/or aromatic carbocyclic group;

$R^2$ represents an optionally substituted saturated and/or aromatic carbocyclic group; or a saturated aliphatic hydrocarbon-based group which is substituted by an optionally substituted aromatic group;

the radicals $R^3$ are as generally defined above or better still the radicals $R^3$ represent, independently of each other, a saturated aliphatic hydrocarbon-based group, which is optionally halogenated and/or optionally interrupted by one or more O or S atoms; a halogen atom; an optionally halogenated ($C_1$-$C_{10}$)alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A sixth preferred subgroup of compounds of the invention consists of the compounds of the formula I in which:

$R^1$ represents an optionally substituted saturated and/or aromatic heterocyclic group;

$R^2$ represents an optionally substituted saturated and/or aromatic carbocyclic group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, which is optionally halogenated and/or optionally interrupted by one or more O or S atoms; a halogen atom; an optionally halogenated ($C_1$-$C_{10}$)alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A seventh preferred subgroup of compounds of the invention consists of the compounds of the formula I in which:

$R^1$ represents an optionally substituted saturated and/or aromatic carbocyclic group; or an optionally substituted saturated and/or aromatic heterocyclic group;

$R^2$ represents an optionally substituted saturated and/or aromatic carbocyclic group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, optionally halogenated and/or optionally interrupted by one or more O or S atoms; a halogen atom; an optionally halogenated ($C_1$-$C_{10}$) alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

An eighth preferred subgroup of compounds of the invention consists of the compounds of the formula I in which:

$R^1$ represents an optionally substituted saturated aliphatic hydrocarbon-based group; an optionally substituted saturated and/or aromatic heterocyclic group;

$R^2$ represents an optionally substituted saturated and/or aromatic carbocyclic group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, optionally halogenated and/or optionally interrupted by one or more O or S atoms; a halogen atom; an optionally halogenated ($C_1$-$C_{10}$) alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted ($C_1$-$C_{10}$)alkyl; or an optionally substituted ($C_6$-$C_{10}$)aryl group.

Among these compounds, the ones that are especially distinguished are the compounds for which $R^2$ represents $C_1$-$C_{10}$ alkyl. The compounds for which $R^2$ represents benzyl are also distinguished.

A ninth subgroup of preferred compounds of the invention consists of the compounds of the formula I in which:

$R^1$ is as generally defined above;

$R^2$ represents an optionally halogenated saturated aliphatic hydrocarbon-based group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, optionally halogenated and/or optionally interrupted by one or more O or S atoms; a halogen atom; an optionally halogenated ($C_1$-$C_{10}$) alkoxy group; a ($C_6$-$C_{10}$)aryl group, which is optionally substituted by one or more radicals G°; a 5- to 7-membered heteroaryl group which comprises one or more hetero atoms chosen from O, N and S and is optionally substituted by one or more radicals G°; di($C_1$-$C_{10}$)alkylamino; ($C_6$-$C_{10}$)aryl($C_1$-$C_{10}$)alkyl, in which aryl is optionally substituted by one or more radicals G°.

Among these compounds, the ones that are more particularly preferred are those for which the radicals $R^3$ independently represent optionally halogenated ($C_1$-$C_{10}$)alkyl; optionally halogenated ($C_1$-$C_{10}$)alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di($C_1$-$C_{10}$)alkylamino.

Preferably, among these compounds, $R^1$ represents optionally substituted $(C_1-C_{10})$alkyl; or an optionally substituted $(C_6-C_{10})$aryl group.

Among these compounds, the ones that are especially distinguished are the compounds for which $R^2$ represents $C_1-C_{10}$ alkyl. The compounds for which $R^2$ represents benzyl are also distinguished.

A tenth subgroup of preferred compounds of the invention consists of the compounds of the formula I in which:

$R^1$ is as generally defined above;

$R^2$ represents an optionally substituted saturated and/or aromatic carbocyclic group; or a saturated aliphatic hydrocarbon-based group substituted by an optionally substituted aromatic group;

the radicals $R^3$ are as generally defined above or better still the radicals $R^3$ represent, independently of each other, a saturated aliphatic hydrocarbon-based group, optionally halogenated and/or optionally interrupted by one or more O or S atoms; a halogen atom; an optionally halogenated $(C_1-C_{10})$ alkoxy group; a $(C_6-C_{10})$aryl group, which is optionally substituted by one or more radicals G°; a 5- to 7-membered heteroaryl group which comprises one or more hetero atoms chosen from O, N and S and is optionally substituted by one or more radicals G°; di$(C_1-C_{10})$alkylamino; $(C_6-C_{10})$aryl$(C_1-C_{10})$alkyl, in which aryl is optionally substituted by one or more radicals G°.

Among these compounds, the ones that are more particularly preferred are those for which the radicals $R^3$ independently represent optionally halogenated $(C_1-C_{10})$alkyl; optionally halogenated $(C_1-C_{10})$alkoxy; a halogen atom; phenyl, which is optionally substituted by one or more radicals G°; optionally substituted heteroaryl, such as pyridine, furan, thiophene, oxazole, thiazole, imidazole, isoxazole, isothiazole or pyrimidine; or di$(C_1-C_{10})$alkylamino.

Preferably, among these compounds, $R^1$ represents optionally substituted $(C_1-C_{10})$alkyl; or an optionally substituted $(C_6-C_{10})$aryl group.

Among these compounds, the ones that are especially distinguished are the compounds for which $R^2$ represents $C_1-C_{10}$ alkyl. The compounds for which $R^2$ represents benzyl are also distinguished.

An eleventh subgroup of compounds of the invention consists of the compounds of the formula I in which:

R represents H or $(C_1-C_{10})$alkyl;

$R^1$ represents optionally halogenated $(C_1-C_{10})$alkyl; or optionally substituted $(C_6-C_{10})$aryl;

$R^2$ represents optionally halogenated $(C_1-C_{10})$alkyl; or benzyl;

$R^3$ represents optionally halogenated $(C_1-C_{10})$alkyl; optionally halogenated $(C_1-C_{10})$alkoxy; or a halogen atom;

Z represents O or $CHR^4$ in which $R^4$ is H or $(C_1-C_{10})$alkyl; and also the pharmaceutically acceptable salts thereof.

Among these compounds, the ones that are especially distinguished are the compounds for which $R^2$ represents optionally halogenated $C_1-C_{10}$ alkyl. Those for which $R^2$ represents benzyl are also distinguished.

A twelfth subgroup of compounds of the invention consists of the compounds of the formula I in which:

$R^1$ represents optionally halogenated $(C_1-C_{10})$alkyl;

$R^3$ represents optionally halogenated $(C_1-C_{10})$alkyl; optionally halogenated $(C_1-C_{10})$alkoxy.

A thirteenth subgroup of compounds of the invention consists of the compounds of the formula I in which:

$R^1$ represents optionally halogenated $(C_1-C_{10})$alkyl;

$R^3$ represents optionally halogenated $(C_1-C_{10})$alkyl; or a halogen atom.

A fourteenth subgroup of compounds of the invention consists of the compounds of the formula I in which:

$R^1$ represents optionally halogenated $(C_1-C_{10})$alkyl;

$R^3$ represents optionally halogenated $(C_1-C_{10})$alkoxy; or a halogen atom.

A fifteenth subgroup of compounds of the invention consists of the compounds of the formula I in which:

$R^1$ represents optionally halogenated $(C_1-C_{10})$alkyl;

$R^3$ represents optionally halogenated $(C_1-C_{10})$alkyl.

A sixteenth subgroup of compounds of the invention consists of the compounds of the formula I in which:

$R^1$ represents optionally halogenated $(C_1-C_{10})$alkyl;

$R^3$ represents optionally halogenated $(C_1-C_{10})$alkoxy.

A seventeenth subgroup of preferred compounds consists of the compounds of the formula I in which:

$R^1$ represents optionally halogenated $(C_1-C_{10})$alkyl;

$R^3$ represents a halogen atom.

An eighteenth subgroup of compounds of the invention consists of the compounds of the formula I in which:

$R^1$ represents optionally substituted $(C_6-C_{10})$aryl;

$R^3$ represents optionally halogenated $(C_1-C_{10})$alkyl; or optionally halogenated $(C_1-C_{10})$alkoxy.

A nineteenth subgroup of compounds of the invention consists of the compounds of the formula I in which:

$R^1$ represents optionally substituted $(C_6-C_{10})$aryl;

$R^3$ represents optionally halogenated $(C_1-C_{10})$alkyl; or a halogen atom.

A twentieth subgroup of compounds of the invention consists of the compounds of the formula I in which:

$R^1$ represents optionally substituted $(C_6-C_{10})$aryl;

$R^3$ represents optionally halogenated $(C_1-C_{10})$alkoxy; or a halogen atom.

A twenty-first subgroup of preferred compounds of the invention consists of the compounds of the formula I in which:

$R^1$ represents optionally substituted $(C_6-C_{10})$aryl;

$R^3$ represents optionally halogenated $(C_1-C_{10})$alkyl;

A twenty-second subgroup of compounds of the invention consists of the compounds of the formula I in which:

$R^1$ represents optionally substituted $(C_6-C_{10})$aryl;

$R^3$ represents optionally halogenated $(C_1-C_{10})$alkoxy.

A twenty-third subgroup of preferred compounds consists of the compounds of the formula I in which:

$R^1$ represents optionally substituted $(C_6-C_{10})$aryl;

$R^3$ represents a halogen atom.

Preferred families of the compounds of the invention are subgroups derived from the preceding subgroups, but in which one or more of the following conditions are satisfied:

i) $R^3$ does not represent a saturated aliphatic hydrocarbon-based group which is optionally halogenated and/or optionally interrupted by one or more O or S atoms;

ii) $R^3$ does not represent an alkyl group;

iii) $R^3$ does not represent an alkoxy group;

iv) $R^3$ does not represent a thioalkoxy group:

v) $R^3$ does not represent a saturated aliphatic hydrocarbon-based group which is optionally halogenated and/or optionally interrupted by one or more O or S atoms;

vi) $R^3$ does not represent a nitro group;

vii) $R^3$ does not represent a cyano group;

viii) $R^3$ does not represent a $(C_6-C_{10})$aryloxy group which is optionally substituted by one or more radicals G°;

ix) $R^3$ does not represent a $(C_6-C_{10})$arylthio group which is optionally substituted by one or more radicals G°;

x) $R^3$ does not represent $(C_1-C_{10})$alkylsulfonyl;

xi) $R^3$ does not represent $(C_6-C_{10})$arylsulfonyl in which aryl is optionally substituted by one or more radicals G°;

xii) $R^3$ does not represent 5- to 7-membered heteroaryl which comprises one or more hetero atoms chosen from O, N and S and is optionally substituted by one or more radicals $G°$;
xiii) $R^3$ does not represent $(C_6-C_{10})$aryloxycarbonyl;
xiv) $R^3$ does not represent $(C_6-C_{10})$arylcarbonylamino;
xv) $R^3$ does not represent $(C_1-C_{10})$alkoxycarbonyl;
xvi) $R^3$ does not represent $(C_1-C_{10})$alkylcarbonylamino;
xvii) $R^3$ does not represent $di(C_1-C_{10})$alkylamino;
xviii) $R^3$ does not represent $(C_6-C_{10})$aryl$(C_1-C_{10})$alkyl in which aryl is optionally substituted by one or more radicals $G°$;
xix) $R^3$ does not represent $(C_6-C_{10})$aryl which is optionally substituted by one or more radicals $G°$;
xx) $R^3$ does not represent $(C_1-C_{10})$alkylcarbonyl; or
xxi) $R^3$ does not represent $(C_3-C_8)$cycloalkyl$(C_1-C_{10})$alkyl in which cycloalkyl is optionally substituted by one or more radicals $G°$.

The invention relates more specifically to all the subgroups listed above.

These subgroups can be divided into three subgroups:
the first defined by $Z=O$;
the second defined by $Z=CH_2$; and
the third defined by $CHR^4$ in which $R^4$ represents optionally halogenated alkyl; preferably $(C_1-C_6)$alkyl.

In a more particularly preferred manner, mention will be made of the following compounds:
(E,E)-6-(2,5-dimethoxyphenyl)-6-oxo-3-methylhexa-2,4-dienoic acid;
ethyl (E,E)-6-(2-methoxy-5-ethylphenyl)-6-oxo-3-methylhexa-2,4-dienoate;
(E,E)-6-(2-methoxy-5-ethylphenyl)-6-oxo-3-methylhexa-2,4-dienoic acid;
ethyl (E,E)-6-(2-methoxy-5-chlorophenyl)-6-oxo-3-methylhexa-2,4-dienoate;
(E,E)-6-(2-methoxy-5-chlorophenyl)-6-oxo-3-methylhexa-2,4-dienoic acid;
(E,E)-6-(2,5-dimethoxyphenyl)-6-oxo-3-phenylhexa-2,4-dienoic acid;
ethyl (E,E)-6-(2,5-dimethoxyphenyl)-6-oxo-3-methylhexa-2,4-dienoate;
ethyl (E,E)-6-(2-benzyloxy-5-methoxyphenyl)-6-oxo-3-methylhexa-2,4-dieonate;
ethyl (E,E)-6-(2,5-dimethoxyphenyl)-6-oxo-3-propylhexa-2,4-dionate;
(E,E)-6-(2,5-dimethoxyphenyl)-6-oxo-3-propylhexa-2,4-dienoic acid;
(E,E)-6-(2-hydroxy-5-methoxyphenyl)-6-oxo-3-methylhexa-2,4-dienoic acid;
ethyl 6-(2-isobutoxy-5-methoxyphenyl)-6-oxo-3-methylhexa-2,4-dienoate; and
6-(2-isobutoxy-5-methoxyphenyl)-6-oxo-3-methylhexa-2,4-dienoic acid.

The compounds of the invention can be prepared by carrying out a process which comprises the reaction of a compound of the formula II:

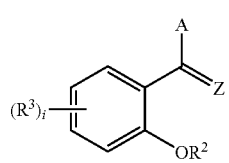

in which i, $R^3$, $R^2$ and Z are as defined above for formula I, with a compound of the formula III:

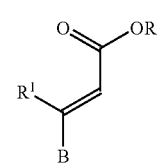

in which $R^1$ and R are as defined above for formula I, except that R does not represent a hydrogen atom, and either A or B represents —CHO, the other representing:

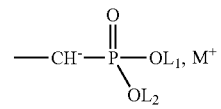

in which $L_1$ and $L_2$ are $(C_1-C_6)$alkyl and $M^+$ represents a monovalent cation.

According to one preferred embodiment of the invention, the salts used as reagents II or III and bearing the function $—CH^-—P(O)(OL_1)(OL_2),M^+$ are prepared in situ from the corresponding compounds bearing the function:

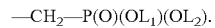

—CH$_2$—P(O)(OL$_1$)(OL$_2$).

A distinction is made between the case in which the salt is a compound of the formula II and the case in which the salt is a compound of the formula III.

If the salt is a compound of the formula II, it can be prepared by the action of a base on the corresponding compound of the formula IIa

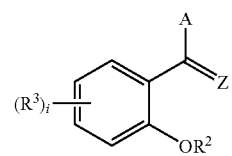

in which
i, $R^3$, $R^2$ and Z are as defined above for formula II and A represents:
—CH$_2$—P(O) (OL$_1$) (OL$_2$) in which $L_1$ and $L_2$ are $(C_1-C_6)$ alkyl.

The base used may be a mineral or organic base. A strong mineral base, such as KOH, NaOH, $K_2CO_3$, $Na_2CO_3$, $KHCO_3$ or $NaHCO_3$ is preferably used.

The base is generally used in excess relative to the amount of compound IIa. In general, a molar ratio of 1 to 5 and preferably of 1 to 4, for example of 1.2 to 3, of the base to the compound of the formula IIa is used.

The reaction is preferably performed in a polar aprotic solvent, such as an ether of the linear or cyclic type. Examples of solvents are diethyl ether, di-tert-butyl ether, dioxane, tetrahydrofuran, diisopropyl ether, dimethoxyethane and diethylene glycol dimethyl ether.

The reaction is generally performed at a temperature of between 20 and 110° C., the temperature depending on the acidity of the proton borne by the carbon α to the —P(O)(OL$_1$)(OL$_2$).

The expected compound of the formula II in which A represents —CH$^-$P(O)(OL$_1$)(OL$_2$), M$^+$ is thus obtained.

According to one preferred embodiment of the invention, this compound is not isolated, and the reaction is continued by adding to the reaction medium a compound of the formula III in which B represents —CHO.

The amount of compound of the formula III added is theoretically the stoichiometric amount. However, it is desirable to perform the process in the presence of a slight excess of the compound of the formula III. Thus, the molar ratio of the compound of the formula III to the compound of the formula II generally ranges between 1 and 5, for example between 1 and 3 and preferably between 1.2 and 1.5.

The reaction of compound II with compound III is thus performed in a solvent that is an ether as defined above.

The reaction temperature generally ranges between 10 and 30° C., for example between 15 and 30° C.

However, at the start of the addition, it is desirable for the temperature of the reaction medium to be lowered to the range from −10° C. to 20° C.

If the salt is a compound of the formula III, it can be prepared by the action of a base on the corresponding compound of the formula IIIa:

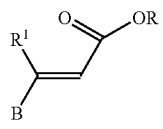

in which R and R$^1$ are as defined above for formula III and B represents —CH$_2$—P(O)(OL$_1$)(OL$_2$) in which L$_1$ and L$_2$ are (C$_1$-C$_6$)alkyl.

The reaction conditions are substantially identical to those recommended above for the formation of compound II from the compound of the formula IIa.

It will be noted that, in the case of the compound of the formula IIIa, a stoichiometric amount of the base is sufficient to form compound III.

Similarly, given the higher reactivity of the compound of the formula IIIa, the anion III can be obtained at room temperature, i.e. at a temperature of between 15 and 30° C.

The compounds of the formula I in which R represents H can be obtained simply from the corresponding compounds of the formula I in which R represents a saturated aliphatic hydrocarbon-based group by saponification using a base, such as one of the mineral bases mentioned above, and this can be performed in a conventional manner.

Sodium and potassium bicarbonate and sodium and potassium hydroxide are preferred.

The saponification reaction can be performed at a temperature of between 50 and 120° C., for example between 60 and 100° C., in an aqueous alcohol, such as a mixture of a lower alkanol and water.

Examples of lower alkanols that may be mentioned include ethanol, methanol and propanol.

A large excess of base is generally used relative to the amount of ester of the formula I used.

By way of example, the molar ratio of the base to the ester of the formula I ranges between 1 and 5 and preferably between 1 and 3.

The compounds of the formula IIa can be prepared by reacting a phosphite of the formula IV:

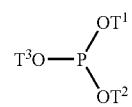

in which T$^1$, T$^2$ and T$^3$ are independently a saturated aliphatic hydrocarbon, such as a (C$_1$-C$_6$)alkyl, with a compound of the formula V:

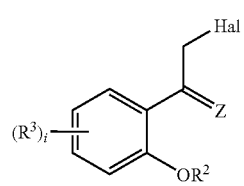

in which R$^3$, i, Z and R$^2$ are as defined above for formula I and Hal represents a halogen atom and more preferably bromine.

Compounds IV and V are advantageously used in stoichiometric amount. The reaction is preferably performed at a temperature from 70 to 200° C., for example from 90 to 160° C. and better still from 110° C. to 150° C.

This reaction can be performed in the absence of a solvent.

If Hal is a bromine atom, the compound of the formula V can be prepared by the action of bromine on a compound of the formula VI:

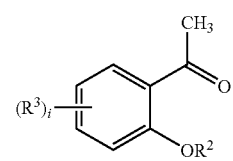

in which R$^3$, i and R$^2$ are as defined above for formula I.

The molar amount of bromine used advantageously ranges between 1 and 1.2 equivalents relative to the amount of compound VI present. A stoichiometric amount is generally sufficient.

The reaction solvent is advantageously a polar aprotic solvent, such as a halogenated aliphatic hydrocarbon or a halogenated aromatic hydrocarbon. A preferred example of a solvent is chloroform. However, other solvents may also be selected, such as a chlorobenzene, carbon tetrachloride or dichloromethane.

The reaction temperature is generally between 20 and 120° C., for example between 40 and 110° C.

The compound of the formula VI can itself be readily prepared from a compound of the formula VII by the action of an alkylating agent:

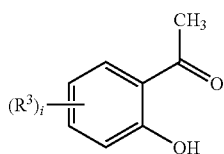

VII in which i and $R^3$ are as defined above.

An alkylating agent that may be mentioned is a halide of the formula VIII $$\text{Hal-}R^2 \qquad \qquad \text{VIII}$$

in which Hal is a halogen atom and $R^2$ is as defined above for formula I.

This alkylation reaction is preferably performed in the presence of a hydride, such as sodium hydride.

The solvent is usually a highly polar aprotic solvent, for instance an amide, such as acetamide or dimethylformamide.

The molar ratio of the hydride to the compound of the formula VII ranges between 1 and 1.5 and better still between 1 and 1.2.

This alkylation reaction is generally performed at a temperature of between 15 and 130° C. and preferably between 20 and 80° C.

The compounds of the formula IIIa can be readily prepared from corresponding compounds of the formula IX:

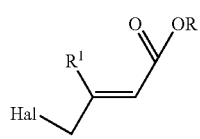

IX in which $R^1$ and R are as defined above for formula IIIa and Hal represents a halogen atom, by the action of a phosphite of the formula X:

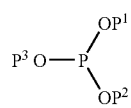

X in which $P^1$, $P^2$ and $P^3$ are $C_1$-$C_6$ alkyl.

Preferably, the molar ratio of the compound of the formula IX to the compound of the formula X ranges between 1 and 1.2 and preferably between 1 and 1.1.

The reaction is advantageously performed in a solvent of linear or cyclic ether type as defined above. A cyclic ether, such as tetrahydrofuran or dioxane will preferably be selected.

The reaction temperature is maintained, for example, between 80 and 140° C., for example between 90 and 120° C.

If Hal is Br, the compound of the formula IX can be obtained by reacting N-bromosuccinimide with the corresponding compound of the formula XV:

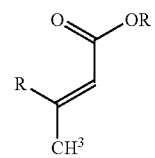

XV in which $R^1$ and R are as defined above for formula I.

The reaction is a free-radical reaction and it is therefore desirable to add to the reaction medium a free-radical-reaction initiator, for instance an azo compound, such as azobisisobutyronitrile or 2,2'-azobis(2-methylpropionitrile) or a peroxide, such as tert-butyl peroxide.

The reaction is preferably performed in carbon tetrachloride.

The amount of initiator is a catalytic amount.

The molar ratio of the N-bromosuccinimide to the compound of the formula XV preferably ranges between 1 and 5, for example between 1 and 3.

The reaction temperature advantageously ranges between 40 and 130° C., for example between 60 and 80° C.

The amount of initiator used is a catalytic amount.

As a variant, the compound of the formula IX can be obtained by reacting a compound of the formula XI:

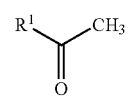

XI in which $R^1$ is as defined above, with a compound of the formula XII

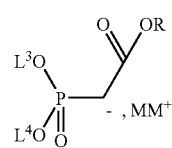

XII in which R is as defined above for formula IX, $L^3$ and $L^4$ independently represent ($C_1$-$C_6$)alkyl, and MM+ represents a monovalent cation.

The compound of the formula XII is obtained by the action of a hydride, such as sodium hydride on the corresponding compound of the formula XIII:

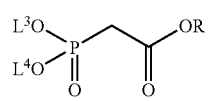

XIII in which R, $L^3$ and $L^4$ are as defined above.

The amount of sodium hydride used generally ranges between 1 and 5 equivalents, for example between 1 and 3 equivalents.

The reaction to form the anion is generally performed in a solvent, such as a linear or cyclic ether.

By way of example, dioxane and tetrahydrofuran are preferred.

The reaction temperature preferably ranges between 30 and 100° C., for example between 40 and 60° C.

If the anion XII is formed by the action of sodium hydride, MM⁺ is the Na⁺ cation.

According to one preferred embodiment of the invention, and, without isolating the intermediate anion XII, the ketone XI is added to the reaction medium, in a molar ratio of the ketone XI to compound XII preferably of between 1 and 1.5 or more generally between 1 and 3.

The addition is preferably performed at low temperature, for example between −10° C. and +20° C. The temperature is then adjusted to between 15 and 40° C.

The compound of the formula II in which A represents —CHO can be prepared by the action of an oxidizing agent, such as selenium oxide on the corresponding compound of the formula XIV:

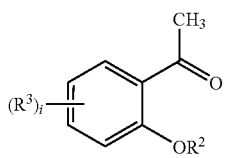

XIV in which i, $R^3$ and $R^2$ are as defined above for formula I.

The reaction is advantageously performed in a mixture of ether and water, the ether being one of the cyclic or linear ethers defined above. A preferred mixture is a mixture of dioxane and water.

The amount of selenium oxide preferably ranges between 1 and 3 equivalents and preferentially between 1 and 1.5 equivalents.

The reaction temperature is, for example, between 30 and 110° C. and better still between 50 and 90° C.

The invention also relates to pharmaceutical compositions comprising a pharmaceutically effective amount of a compound of the formula (I) as defined above in combination with one or more pharmaceutically acceptable vehicles.

These compositions can be administered orally in the form of tablets, gel capsules or granules with immediate release or sustained release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule may be suitably coated with sugar, gelatine or the like.

An injectable form comprising the compound of the present invention as active principle is prepared, where appropriate, by mixing the said compound with a pH regulator, a buffer agent, a suspension agent, a solubilizer, a stabilizer, an isotonic agent and/or a preserving agent, and by converting the mixture into a form for intravenous, subcutaneous or intramuscular injection, according to a standard process. Where appropriate, the injectable form obtained may be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80, nicotinamide, polyethoxylated sorbitan monolaurate and the ethyl ester of castor oil fatty acid.

In addition, the stabilizer encompasses sodium sulfite, sodium metasulfite and ether, while the preserving agent encompasses methyl p-hydroxybenzoate, ethyl p-hydroxybenzoate, sorbic acid, phenyl [sic], cresol and chlorocresol.

The invention is also directed towards the use of an active principle chosen from a compound of the formula (I) as defined above, for the preparation of a medicament intended for the prevention of or treating dyslipidaemia, atherosclerosis and diabetes.

The compounds of the invention are preferably administered at doses ranging from about 0.1 to 100 mg and in particular between 1 and 10 mg per dosage unit.

The daily dosage is preferably between 0.001 and 10 mg per kg of body weight.

Nevertheless, in the case of each patient, the effective dose depends on various factors, such as the efficacy of the specific compound administered, the age, body weight, general state of health and sex of the patient, the diet followed, the route of administration, the dosage regimen followed, the rate of excretion of the active principle, possible pharmaceutical combinations and the severity of the particular disorder to be treated.

The compounds of the invention are advantageously administered orally.

The measurement of the PPAR activation was performed according to a technique described by Lehmann et al. (1995, J. Biol. Chem. 270: 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter containing Gal4 response elements.

The cells are inoculated in 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced by whole medium comprising the test products (50 μM final).

The products are left in contact with the cells for 18 hours. The cells are then lysed and the luciferase activity is measured using a luminometer. A PPAR activation factor can then be calculated by means of the activation of the expression of the reporter gene induced by the product (relative to the control cells that have not received any product).

By way of example, ethyl 6-(2,5-dimethoxyphenyl)-6-oxo-3-propylhexa-2,4-dienoate at a concentration of 50 μM, activates the chimeric protein PPARγ-Gal4 by factor of five, and the chimeric protein PPARα-Gal4 by a factor of seven. In the absence of the binding region for the PPAR α or γ ligand (vector expressing Gal4 alone), the luciferase activity measured in the presence of this product is zero.

The examples that follow illustrate invention in a non-limiting manner.

In the proton nuclear magnetic resonance (NMR) data, the following abbreviations have been used: s for singlet, d for doublet, t for triplet, q for quartet, o for octet and m for complex multiplet. The chemical shifts δ are expressed in ppm; m.p. represents the melting point and b.p. represents the boiling point.

EXAMPLES

Example 1

Step a): 1-(2-isobutoxy-5-methoxyphenyl)ethanone

A mixture of 10 g (0.06 mol) of 2'-hydroxy-5'-methoxyacetophenone, 2.6 g (0.066 mol) of 60% sodium hydride and 150 ml of dimethylformamide is heated for one hour at 80° C. 7.2 ml (0.066 mol) of 1-bromo-2-methylpropane are added dropwise. The mixture is heated for ten hours at 80° C. and is then poured into ice-water and extracted with ether. The ether solution is washed with normal sodium hydroxide solution. The dried ($Na_2SO_4$) organic phase is evaporated under reduced pressure (8.2 g; 62%).

Step b): 2-bromo-1-(2-isobutoxy-5-methoxyphenyl))ethanone 2.1 ml (0.045 mol) of bromine are added dropwise to a solution of 10 g (0.045 mol) of 1-(2-isobutoxy-5-methoxyphenyl))ethanone in 100 ml of refluxing carbon tetrachloride. Heating is continued for one hour at the reflux point of carbon tetrachloride. After washing with water and drying the organic phase ($Na_2SO_4$), the solvent is evaporated off under reduced pressure (15 g). The residue is purified by flash chromatography (70/30 heptane/dichloromethane) (11.7 g of yellow solid recrystallized from diisopropyl ether; 73%).

Step c): ethyl [2-(2-isobutoxy-5-methoxyphenyl)-2oxoethyl]phosphonate

A mixture of 8 g (0.0266 mol) of 2-bromo-1-(2-isobutoxy-5-methoxyphenyl))ethanone and 4.6 ml (0.0266 mol) of triethyl phosphate is heated at 140° C. After cooling, the product is purified by flash chromatography (40/60 heptane/ethyl acetate) (3.2 g; 34%).

Step d): ethyl 6-(2-isobutoxy-5-methoxyphenyl)-6-oxo-3-methylhexa-2,4-dienoate 3 g (8.4 mmol) of ethyl [2-(2-isobutoxy-5-methoxyphenyl)-2-oxoethyl]-phosphonate dissolved in 20 ml of tetrahydrofuran are added dropwise to a suspension of 1.41 g (12.6 mmol) of potassium tert-butoxide in 30 ml of tetrahydrofuran, heated to 50° C. Heating is continued for 20 minutes at 50° C., the mixture is then cooled to 0° C. and 1.8 g (12.6 mmol) of ethyl 3-methyl-4-oxocrotonate dissolved in 20 ml of tetrahydrofuran are added dropwise. The reaction mixture is then stirred for 72 hours at 25° C. Water is added and the resulting mixture is extracted with ether. After drying ($Na_2SO_4$), the solvent is evaporated off and the residue is purified by flash chromatography (dichloromethane) (2.58 g of yellow oil; 89%).

$^1$H NMR ($CDCl_3$): 0.99 (6H, d, J=6.78 Hz); 1.30 (3H, t, J=7.16 Hz); 2.06 (1H, m); 2.32 (3H, m); 3.74 (2H, d, J=6.41 Hz); 3.79 (3H, s); 4.20 (2H, q, J=7.16 Hz); 6.09 (1H, m); 6.88 (1H, m); 7.01 (1H, m); 7.18 (1H, m); 7.28 (2H, m).

Example 2

6-(2-Isobutoxy-5-methoxyphenyl)-6-oxo-3-methyl-hexa-2,4-dienoic acid 1 g (2.9 mmol) of ethyl 6-(2-isobutoxy-5-phenyl)-6-oxo-3-methylhexa-2,4-enoate, 30 ml of ethanol, 0.24 g of potassium hydroxide and 10 ml of water are mixed together and refluxed for three hours. After evaporating off the solvents, the residue is poured into water, acidified with normal hydrochloric acid solution and extracted with ether. The organic phase is dried ($Na_2SO_4$), the solvent is evaporated off and the pasty product obtained is recrystallized (10/6 hexane/ethyl acetate) (0.3 g of yellow solid; 33%).

$^1$H NMR ($CDCl_3$): 0.99 (6H, d, J=6.78 Hz); 2.06 (1H, m); 2.35 (3H, m); 3.75 (2H, d, J=6.78 Hz); 3.79 (3H, s); 6.13 (1H, m); 6.89 (1H, m); 7.02 (1H, m); 7.19 (1H, m); 7.22-7.41 (2H, m).

N. B.: H-acid not observed.

Example 3

Step a): (2,5-dimethoxyphenyl)-2-oxoacetaldehyde

A mixture of 3.66 g (33 mmol) of selenium dioxide, 1 ml of water and 25 ml of dioxane is heated to 60° C. 5.4 g (30 mmol) of 2',5'-dimethoxyacetophenone are added and the mixture is refluxed for 16 hours. The solvents are evaporated off (orange-coloured oil; 6 g) and the product obtained is purified by flash chromatography (dichloromethane) (3.1 g of yellow oil; 53%).

Step b): ethyl (E)-3-phenylbut-2-enoate

A mixture of 10 g (0.25 mol) of sodium hydride and tetrahydrofuran is heated to 50° C., followed by dropwise addition over 30 minutes of a solution of 48 ml (0.19 mol) of ethyl diethylphosphonoacetate in 80 ml of tetrahydrofuran. A solution of 28.4 g (0.24 mol) of acetophenone in 60 ml of tetrahydrofuran is added dropwise at 0° C. and the mixture is stirred for 16 hours at 25° C. 250 ml of saturated sodium chloride solution are added at 0° C. and the resulting mixture is extracted with ether. The organic phase is dried ($Na_2SO_4$) and the solvents are evaporated off under reduced pressure. The 46.6 g of product obtained are purified by flash chromatography (90/10 cyclohexane/diisopropyl ether) (29 g; 63%).

Step c): ethyl (E)-4-bromo-3-phenylbut-2-enoate

A mixture of 14 g (74 mmol) of ethyl (E)-3-phenylbut-2-enoate, 0.47 g of 2,2'-azobis(2-methylpropionitrile) and 330 ml of carbon tetrachloride is heated to 75° C. 19.8 g (111 mmol) of N-bromosuccinimide are added portionwise at this temperature. The mixture is then refluxed for five hours. The insoluble material is filtered off at 25° C. The filtrate is washed with water and dried over $Na_2SO_4$; the solvents are evaporated off (orange-coloured oil: 19.7 g; 99%).

Step d): ethyl (E)-4-(diethoxyphosphoryl)-3-phenyl-but-2-enoate

A mixture of 14.6 g (0.054 mol) of ethyl (E)$_4$-bromo-3-phenylbut-2-enoate, 9.6 g (0.058 mol) of triethylphosphine and 200 ml of dioxane is heated at 100° C. for 11 hours. Water is added and the mixture is extracted with dichloromethane. The organic phase is separated out by settling and dried over Na$_2$SO$_4$. The solvents are evaporated off (orange-coloured oil; 19.5 g) and the product is purified by flash chromatography (ethyl acetate) (13.7 g; 78%).

Step e): ethyl (2Z, 4E)-6-(2,5-dimethoxyphenyl)-6-oxo-3-phenylhexa-2,4-dienoate 1.32 g (11.8 mmol) of potassium tert-butoxide and 30 ml of tetrahydrofuran are mixed together at 25° C. A solution of 3.85 g (11.8 mmol) of ethyl (E)-4-(diethoxyphosphoryl)-3-phenylbut-2-enoate in 30 ml of tetrahydrofuran is then added dropwise. A solution of 3 g (15.4 mmol) of (2,5-dimethoxyphenyl)-2-oxoacetaldehyde dissolved in 30 ml of tetrahydrofuran is added dropwise, at 25° C. The mixture is stirred for 16 hours at 25° C. It is poured into water and extracted with ether. The organic phase is dried (Na$_2$SO$_4$) and the solvents are evaporated off under reduced pressure. The 4 g of product obtained are purified by flash chromatography (80/20 heptane/ethyl acetate) (yellow oil: 0.46 g).

Step f): (2Z, 4E)-6-(2,5-dimethoxyphenyl)-6-oxo-3-phenylhexa-2,4-dienoic acid 0.45 g (1.22 mmol) of ethyl (2Z, 4E)-6-(2,5-dimethoxyphenyl)-6-oxo-3-phenylhexa-2,4-dienoate, 20 ml of ethanol, 0.206 g (2.44 mmol) of sodium bicarbonate and 20 ml of water are mixed together and refluxed for three hours. After evaporating off the solvents, the residue is poured into water, acidified with normal hydrochloric acid solution and extracted with dichloromethane. The organic phase is dried (Na$_2$SO$_4$), the solvent is evaporated off and the pasty product obtained is purified by flash chromatography (20/80 heptane/ethyl acetate) (yellow solid; diisopropyl ether; m.p.: 165° C.; 170 mg) and recrystallized (10/6 hexane/ethyl acetate) (0.3 g of yellow solid; 22%).

$^1$H NMR-CHCl$_3$-δ(ppm): (98 765-98792)

Examples 4 to 9

Using a procedure similar to one of those illustrated above, the compounds in the table below were prepared:

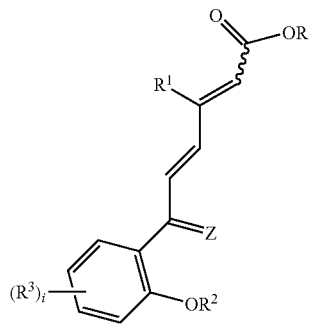

| Example No. | R$^3$ | i | R$^2$ | Z | R$^1$ | R | NMR |
|---|---|---|---|---|---|---|---|
| 4 | 5-OCH$_3$ | 1 | —CH$_3$ | O | —CH$_3$ | —H | (CDCl$_3$): 2.38 (3H, m); 3.80 (3H, s); 3.85 (3H, s); 6.12 (1H, m); 6.93 (1H, m); 7.05 (1H, m); 7.15-7.30 (3H, m) N.B., : H-acid not observed. |
| 5 | 5-Et | 1 | —CH$_3$ | O | —CH$_3$ | —Et | (CDCl$_3$): 1.21 (3H, m); 1.29 (3H, m); 2.34 (3H, m); 2.61 (2H, m); 3.86 (3H, s); 4.19 (2H, m); 6.07 (1H, m); 6.90 (1H, m); 7.15-7.22 (2H, m); 7.27-7.48 (2H, m). |
| 6 | 5-Et | 1 | —CH$_3$ | O | —CH$_3$ | —Et | (DMSO-d6): 1.15 (3H, m); 2.24 (3H, m); 2.57 (2H, m); 3.83 (3H, s); 6.20 (1H, m); 7.03-7.19 (3H, m); 7.33 (1H, m); 7.39 (1H, m); 12.51 (1H, broad s). |
| 7 | 5-Cl | 1 | —CH$_3$ | O | —CH$_3$ | —Et | (CDCl$_3$): 1.29 (3H, m); 2.33 (3H, m); 3.87 (3H, s); 4.19 (2H, m); 6.08 (1H, m); 6.92 (1H, m); 7.03-7.26 (2H, m); 7.41 (1H, m); 7.56 (1H, m). |

-continued

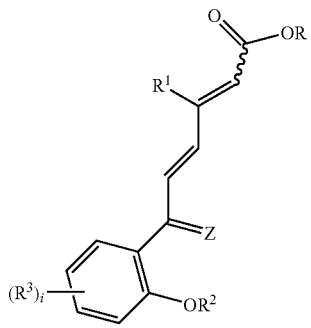

| Example No. | R³ | i | R² | Z | R¹ | R | NMR |
|---|---|---|---|---|---|---|---|
| 8 | 5-Cl | 1 | —CH₃ | O | —CH₃ | —H | (DMSO-d6): 2.23 (3H, m); 3.86 (3H, s); 6.23 (1H, m); 7.07 (1H, m); 7.14-7.27 (2H, m); 7.48 (1H, m); 7.59(1H, m); 12.58 (1H, broad s). |
| 9 | 5-OCH₃ | 1 | —CH₃ | O | —C₆H₅ | —H | (CDCl₃): 3.76 (3H, s); 3.80 (3H, s); 6.16-6.35 (2H, m); 6.85 (1H, m); 7.04 (1H, m); 7.21-7.35 (3H, m); 7.49 (4H, m). N.B, : H-acid not observed. |
| 10 | 5-OCH₃ | 1 | —CH₃ | O | —CH₃ | —Et | (CDCl₃): 1.16-1.40 (3H, m); 1.55 (3H, s); 3.79 (3H, s); 3.84 (3H, s); 4.09-4.29 (2H, m); 6.08 (1H, s); 6.87-6.97 (1H, m); 6.98-7.09 (1H, m); 7.11-7.34 (3H, m). |
| 11 | 5-OCH₃ | 1 | —CH₂C₆H₅ | O | —CH₃ | —Et | (CDCl₃): 1.22-1.42 (3H, m); 2.0 (3H, s); 3.82 (3H, s); 4.13-4.28 (2H, m); 5.08 (2H, s); 6.05 (1H, s); 6.97-7.12 (2H, m); 7.22-7.47 (8H, m). |
| 12 | 5-OCH₃ | 1 | —CH₃ | O | —CH₂—CH₂—CH₃ | —Et | (CDCl₃): 0.88-1.10 (3H, m); 1.17-1.40 (3H, m); 1.45-1.70 (2H, m); 2.68-2.92 (2H, m); 3.80 (3H, s); 3.84 (3H, s); 4.06-4.28 (2H, m); 6.05 (1H, s); 6.80-7.35 (5H, m). |
| 13 | 5-OCH₃ | 1 | —CH₃ | O | —CH₂—CH₂—CH₃ | —H | (DMSO-d6): 0.79-1.04 (3H, m); 1.35-1.61 (2H, m); 2.62-2.86 (2H, m); 3.73 (3H, s); 3.81 (3H, s); 6.18 (1H, s); 6.92-7.26 (5H, m); 12.54 (1H, broad s). |
| 14 | 5-OCH₃ | 1 | —H | O | —CH₃ | —H | (CDCl₃): 1.57 (1H, broad s); 2.43 (3H, s); 3.83 (3H, s); 6.21 (1H, s); 6.93-7.02 (1H, m); 7.09-7.30 (2H, m); 7.30-7.56(2H, m); 12.10 (1H, s). |

The invention claimed is:
1. A compound that is:
(E,E)-6-(2,5-dimethoxyphenyl)-6-oxo-3-methylhexa-2,4-dienoic acid;
ethyl (E,E)-6-(2-methoxy-5-ethylphenyl)-6-oxo-3-methylhexa-2,4-dienoate;
(E,E)-6-(2-methoxy-5-ethylphenyl)-6-oxo-3-methylhexa-2,4-dienoic acid;

ethyl (E,E)-6-(2-methoxy-5-chlorophenyl)-6-oxo-3-methylhexa-2,4-dienoate;

(E,E)-6-(2-methoxy-5-chlorophenyl)-6-oxo-3-methylhexa-2,4-dienoic acid;

(E,E)-6-(2,5-dimethoxyphenyl)-6-oxo-3-phenylhexa-2,4-dienoic acid;

ethyl (E,E)-6-(2,5-dimethoxyphenyl)-6-oxo-3-methylhexa-2,4-dienoate;

ethyl (E,E)-6-(2-benzyloxy-5-methoxyphenyl)-6-oxo-3-methylhexa-2,4-dieonate;

ethyl (E,E)-6-(2,5-dimethoxyphenyl)-6-oxo-3-propylhexa-2,4-dionate;

(E,E)-6-(2,5-dimethoxyphenyl)-6-oxo-3-propylhexa-2,4-dienoic acid;

(E,E)-6-(2-hydroxy-5-methoxyphenyl)-6-oxo-3-methylhexa-2,4-dienoic acid;

ethyl 6-(2-isobutoxy-5-methoxyphenyl)-6-oxo-3-methylhexa-2,4-dienoate; or 6-(2-isobutoxy-5-methoxyphenyl)-6-oxo-3-methylhexa-2,4-dienoic acid.

2. A pharmaceutical composition comprising one or more compounds according to claim 1, in combination with one or more pharmaceutically acceptable excipients.

3. A method for the treatment of dyslipidaemia, atherosclerosis or diabetes comprising administering to a patient in need thereof an effective amount of a compound according to claim 1.

* * * * *